(12) United States Patent
Masui et al.

(10) Patent No.: US 8,168,580 B2
(45) Date of Patent: May 1, 2012

(54) METHOD FOR PRODUCING AQUEOUS α-SULFO FATTY ACID ALKYL ESTER SALT SOLUTION

(75) Inventors: Hiroyuki Masui, Tokyo (JP); Kensuke Itakura, Kawaguchi (JP); Hiroshi Gotou, Ichikawa (JP)

(73) Assignee: Lion Corporation, Sumida-ku, Tokyo (JP)

( * ) Notice: Subject to any disclaimer, the term of this patent is extended or adjusted under 35 U.S.C. 154(b) by 0 days.

(21) Appl. No.: 13/129,867

(22) PCT Filed: Nov. 20, 2009

(86) PCT No.: PCT/JP2009/006282
§ 371 (c)(1),
(2), (4) Date: May 18, 2011

(87) PCT Pub. No.: WO2010/058599
PCT Pub. Date: May 27, 2010

(65) Prior Publication Data
US 2011/0230389 A1    Sep. 22, 2011

(30) Foreign Application Priority Data

Nov. 21, 2008    (JP) .................................. 2008-298469

(51) Int. Cl.
*C11D 17/00* (2006.01)
(52) U.S. Cl. .......... 510/426; 510/427; 510/429; 510/492
(58) Field of Classification Search .................. None
See application file for complete search history.

(56) References Cited

FOREIGN PATENT DOCUMENTS

| JP | 61-280467 | | 12/1986 |
|---|---|---|---|
| JP | 62-116698 | | 5/1987 |
| JP | 3-101828 | | 4/1991 |
| JP | 3-1018128 | * | 4/1991 |
| JP | 3-106436 | | 5/1991 |
| JP | 9-12532 | | 1/1997 |
| JP | 9-75786 | | 3/1997 |
| JP | 2003-82395 | | 3/2003 |
| JP | 2007-320978 | | 12/2007 |

OTHER PUBLICATIONS

International Search Report for International Application No. PCT/JP2009/006282 mailed Feb. 2, 2010 (Form PCT/ISA/210).

* cited by examiner

*Primary Examiner* — Necholus Ogden, Jr.
(74) *Attorney, Agent, or Firm* — Merchant & Gould P.C.

(57) ABSTRACT

The present invention relates to a method for producing an aqueous α-SF salt solution that maintains fluidity and has superior production adaptability. The method includes dissolving a solid component (a) in the form of an α-sulfo fatty acid alkyl ester salt and a component (b) in the form of an inorganic sodium salt and/or inorganic potassium salt in water, wherein component (a) is dissolved in water at a temperature of 50° C. or higher while maintaining the following condition (i) or (ii):

(i): the concentration of component (a) is 35% by weight or less when the total concentration of sodium and potassium ions derived from component (b) is less than 0.55 mol/kg, or (ii) the concentration of component (a) is 55% by weight or less when the total concentration of sodium and potassium ions derived from component (b) is 0.55 mol/kg to less than 1.8 mol/kg.

4 Claims, 3 Drawing Sheets

METHOD FOR PRODUCING AQUEOUS α-SULFO FATTY ACID ALKYL ESTER SALT SOLUTION

This application is a National Stage Application of International Application No. PCT/JP2009/006282, filed 20 Nov. 2009, which claims the benefit of Japanese Patent Application No. 2008-298469, filed 21 Nov. 2008 in Japan, the disclosures of all of which are hereby incorporated by reference in their entireties. To the extent appropriate, a claim of priority is made to each of the above disclosed applications. The International Application was published in Japanese on 27 May 2010 as WO 2010/058599.

The present invention relates to a method for producing an aqueous α-sulfo fatty acid alkyl ester salt solution.

BACKGROUND

Since α-sulfo fatty acid alkyl ester salts (to be simply referred to as "α-SF salts") demonstrate high cleaning strength, have favorable biodegradability and have little impact on the environment, their performance as detergent materials is evaluated highly. In addition, they are also advantageous in terms of costs in recyclable natural raw material systems in terms of resources as well, and are viewed with importance in terms of protecting the global environment as well.

A typical example of a method for producing α-SF salts consists of sulfonating a fatty acid alkyl ester using $SO_3$ gas and the like to obtain an α-sulfo fatty acid alkyl ester (to be referred to as "α-SF"), followed by neutralizing with base to obtain an α-SF-containing aqueous solution in the form of a liquid or paste.

However, α-SF-containing aqueous solutions as described above increase in viscosity as the α-SF salt concentration increases resulting in the formation of a gel that lacks fluidity. When in a state such as this that lacks fluidity, transport by truck or ship becomes difficult, while dilute α-SF-containing aqueous solutions that are able to maintain fluidity result in the incurrence of transportation costs. Consequently, α-SF salts are typically distributed in solid form such as flakes or pellets.

In the production of granulated detergents, a solid α-SF salt as described above is dissolved in water to obtain an aqueous α-SF salt solution, and the aqueous α-SF salt solution is spray-dried with a detergent slurry composed of powdered raw materials, or powdered raw materials are granulated by using the aqueous α-SF salt solution as a binder. Consequently, aqueous α-SF salt solutions preferably have as high an α-SF salt concentration as possible while still maintaining fluidity. On the other hand, if the α-SF salt concentration becomes excessively high, the aqueous α-SF salt solution gels during production, which can cause blockage of flow paths of production equipment or adhere to heat-conducting surfaces causing a decrease in heat transfer efficiency. Methods have been previously reported that attempt to decrease the viscosity of aqueous α-SF salt solutions in order to resolve this problem.

For example, Patent Document 1 describes that the fluidity of an aqueous solution of an α-SF salt can be improved by blending specific amounts of an α-SF salt, an α-sulfo fatty acid disalt and an inorganic sulfate. Patent Document 2 describes a method for improving the fluidity of a surfactant slurry by incrementally concentrating a surfactant slurry containing an α-SF salt in the presence of sodium sulfate. Patent Document 3 describes that an aqueous α-SF salt solution facilitating easier handing by having an α-SF salt concentration of 30 to 60% by weight is obtained by using an inorganic sulfate as an essential component thereof. Patent Document 4 describes that an aqueous α-SF salt solution having favorable fluidity and an α-SF salt concentration of 40% by weight or more is obtained by containing an inorganic chloride. Patent Document 5 describes that an aqueous α-SF salt solution having an α-SF salt concentration of 30 to 60% by weight that facilitates easier handling is obtained by containing an inorganic sulfate and polyoxyalkylene-added polyvalent alcohol.

PATENT DOCUMENTS

[Patent Document 1] Japanese Unexamined Patent Application, First Publication No. H3-101828
[Patent Document 2] Japanese Unexamined Patent Application, First Publication No. 2003-82395
[Patent Document 3] Japanese Unexamined Patent Application, First Publication No. S61-280467
[Patent Document 4] Japanese Unexamined Patent Application, First Publication No. 2007-320978
[Patent Document 5] Japanese Unexamined Patent Application, First Publication No. S62-116698

SUMMARY OF THE INVENTION

Problems to be Solved by the Invention

However, in the case of producing an aqueous α-SF salt solution by dissolving a solid α-SF salt in water, the effects of the decrease in fluidity and gelling accompanying a decrease in the α-SF salt concentration appear more prominently in comparison with the case of concentrating an aqueous α-SF salt solution. Consequently, it is difficult to apply the inventions described in Patent Documents 1 and 2 to a method for producing an aqueous α-SF salt solution that uses a solid α-SF salt. Moreover, from the viewpoint of producing an aqueous α-SF salt solution at the industrial level, the inventions described in Patent Documents 3 to 5 have the risk of being unable to effectively prevent gelling during production of an aqueous α-SF salt solution and being unable to stably maintain fluidity at a level suitable for production.

Therefore, an object of the present invention is to provide a method for producing an aqueous α-SF salt solution that facilitates dissolution of a solid α-SF salt in water even at the industrial level while also maintaining fluidity and having superior production adaptability.

Means for Solving the Problems

The method for producing an aqueous α-SF salt solution of the present invention is a method for producing an aqueous α-sulfo fatty acid ester salt solution in which a solid component (a) in the form of an α-sulfo fatty acid alky ester salt and a component (b) in the form of an inorganic sodium salt and/or inorganic potassium salt are dissolved in a solvent in the form of water; wherein, the solid component (a) is dissolved in the solvent in the form of water under temperature conditions of 50° C. or higher while maintaining the following condition (i) or (ii):

(i): the concentration of the component (a) is 35% by weight or less in the case the total concentration of sodium ions and potassium ions derived from the component (b) is less than 0.55 mol/kg, or (ii): the concentration of the component (a) is 55% by weight or less in the case the total concentration of sodium ions and potassium ions derived from the component (b) is 0.55 mol/kg to less than 1.8 mol/kg.

Moreover, the solid component (a) may also be dissolved in a solvent while maintaining the following condition (iii):

(iii) the concentration of the component (a) is within a range represented by the following formula (1) in the case the total concentration of sodium ions and potassium ions derived from the component (b) is 1.8 mol/kg to less than 4.3 mol/kg:

$$y \leq \leq 22x + 95 \quad (1)$$

(wherein, y represents the concentration of the component (a) (wt %), and x represents the total concentration of sodium ions and potassium ions derived from the component (b) (mol/kg)).

The method for producing an aqueous α-SF salt solution of the present invention preferably consists of using 20% by weight or more of the solvent as the initial solvent, and after dissolving at least a portion of the solid component (a) and component (b) in the initial solvent, adding the remainder of the solvent and finally dissolving the remainder of the solid component (a) and component (b), and the relative addition rate of the solid component (a) to the solvent as represented by the following formula (2) is preferably 0.1 h$^{-1}$ to less than 10 h$^{-1}$.

Relative addition rate of solid component (a)=addition rate of solid component (a) (kg/h)/final amount of aqueous α-sulfo fatty acid alkyl ester salt solution (kg) (2)

Effects of the Invention

According to the method for producing an aqueous α-SF salt solution of the present invention, dissolution of a solid α-SF salt in water is facilitated, and an aqueous α-SF salt solution can be obtained that has superior production adaptability by maintaining fluidity.

DETAILED DESCRIPTION OF THE INVENTION

<Aqueous α-SF Salt Solution>

The aqueous α-SF salt solution obtained with the method for producing an aqueous α-SF salt solution of the present invention is an aqueous solution that contains an α-SF salt and an inorganic sodium salt and/or inorganic potassium salt.

[Component (a): α-SF Salt]

The component (a) is an α-SF salt. The α-SF salt is a salt of a sulfonation product of a fatty acid alkyl ester, and is typically represented by the following general formula (I):

[Chemical Formula 1]

(I)

(wherein, R$^1$ represents a linear or branched alkyl group or alkenyl group having 6 to 22 carbon atoms, R$^2$ represents a linear or branched alkyl group having 1 to 6 carbon atoms, and M represents a counter ion).

An alkyl group of R$^1$ in the formula (I) may be linear or branched, has 6 to 22 carbon atoms, preferably has 10 to 16 carbon atoms, and more preferably has 12 to 16 carbon atoms. An alkenyl group of R$^1$ may be linear or branched, has 6 to 22 carbon atoms, preferably has 10 to 16 carbon atoms, and more preferably has 12 to 16 carbon atoms. R$^1$ is particularly preferably in alkyl group. Namely, the α-SF salt is preferably an α-sulfo saturated fatty acid alkyl ester salt.

An alkyl group of R$^2$ in the formula (I) may be linear or branched, has 1 to 6 carbon atoms, and more preferably has 1 carbon atom. Namely, the α-SF salt is preferably an α-sulfo fatty acid methyl ester.

A counter ion represented by M is that which forms a water-soluble salt with R$^1$—CH(CO—O—R$^2$)—SO$_3$— (wherein, R$^1$ and R$^2$ are the same as R$^1$ and R$^2$ in the formula (I)). Examples of the water-soluble salts include alkaline metal salts such as sodium salts or potassium salts, alkaline earth metal salts such as calcium salts, ammonium salts, and ethanolamine salts. In particular, the water-soluble salt is preferably an alkaline metal salt and more preferably a sodium salt.

An example of such an α-SF salt is a sodium salt of an α-sulfo fatty acid methyl ester (MES).

The concentration of the component (a) in the aqueous α-SF salt solution can be determined according to the concentration of the component (b), and for example, is preferably 30% by weight or more, more preferably 30 to 55% by weight, even more preferably 30 to 53% by weight, and particularly preferably 30 to 50% by weight. This is because if the concentration of the component (a) is within the above ranges, the effects of controlling fluidity of the aqueous α-SF salt solution and solubility of the α-SF salt are prominently demonstrated, and spray-drying and granulation in the production of a granular detergent can be carried out efficiently.

The α-SF salt can be produced according to a known method. For example, an α-SF salt-containing paste is obtained by sulfonating a fatty acid alkyl to obtain a sulfonation product containing α-SF (sulfonation step), followed by esterifying the sulfonation product (esterification step) and subsequently neutralizing to obtain an α-SF salt neutralization product (neutralization step) followed by bleaching (bleaching step). This α-SF salt-containing paste can then be concentrated as necessary to obtain an α-SF salt-containing concentrate (to be simply referred to as a "concentrate") containing a solid α-SF salt. This concentrate can then be subjected to molding and cooling treatment to obtain a solid α-SF salt-containing product in the form of flakes or pellets. Moreover, the solid α-SF salt-containing product in the form of flakes or pellets can then be subjected to crushing treatment to obtain a solid α-SF salt-containing product in the form of a powder and the like. The solid α-SF salt-containing product may also contain α-sulfo fatty acid dialkaline salts produced as by-products and inorganic sulfates and the like used as coloring prevention agents in the α-SF salt production process in addition to the α-SF salt of component (a). This solid α-SF salt-containing product can be preferably used as a supply source of the solid component (a) in the present invention.

The fatty acid alkyl ester is preferably a saturated fatty acid alkyl ester, and may be an animal fat-based alkyl ester derived from beef tallow, fish oil or lanolin, a vegetable oil-based alkyl ester derived from coconut oil, palm oil or soybean oil, or a synthetic fatty acid-based alkyl ester derived from an α-oxo method.

Examples of such fatty acid alkyl esters include methyl, ethyl or propyl laurate, methyl, ethyl or propyl myristate, methyl, ethyl or propyl palmitate, methyl, ethyl or propyl stearate, methyl, ethyl or propyl hardened beef tallow fatty acid, methyl, ethyl or propyl hardened fish oil fatty acid, methyl, ethyl or propyl coconut oil fatty acid, methyl, ethyl or propyl palm oil fatty acid, and methyl, ethyl or propyl palm kernel oil fatty acid.

A known method can be used for the sulfonation step, and for example, a sulfonation product of a fatty acid containing α-SF can be obtained by contacting a sulfonating gas such as $SO_3$ gas or fuming sulfuric acid with a fatty acid alkyl ester. Any sulfonation method such as thin film sulfonation or batch sulfonation may be used for the sulfonation method.

In the esterification step, an esterification product is obtained by adding a lower alcohol to the sulfonation product obtained in the sulfonation step and allowing an esterification reaction to proceed. The formation of by-products is inhibited and the purity of the α-SF is improved by carrying out the esterification step.

In the neutralization step, an α-SF salt-containing neutralization product (to be simply referred to as a "neutralization product") is obtained by neutralizing the esterification product obtained in the esterification step by adding and mixing a base. The neutralization step is preferably carried out under conditions such that the reaction mixture of the base and esterification product is either acidic or weakly basic, namely is within the range of pH 4 to 9.

Examples of bases used in the neutralization step include alkaline metals, alkaline earth metals, ammonia and ethanolamine. These bases are normally used in the form of aqueous solutions, and the concentrations thereof are about 2 to 50% by weight.

In the bleaching step, the α-SF salt-containing neutralization product obtained in the neutralization step is subjected to bleaching treatment using a bleaching agent such as hydrogen peroxide or hypochlorite. A known method can be used for the bleaching treatment, and bleaching treatment can be carried out by, for example, adding and mixing an arbitrary amount of a bleaching agent into the neutralization product.

Concentration of the α-SF salt-containing paste can be carried out according to a known method, and a concentrate can be obtained by, for example, using a thin film vacuum evaporator.

[Component (b): Inorganic Sodium Salt and/or Inorganic Potassium Salt]

Component (b) is an inorganic sodium salt or inorganic potassium salt.

The inorganic sodium salt may be that which is ordinarily incorporated as a detergent component, and examples include sodium sulfate, sodium sulfite, sodium chloride, sodium bicarbonate and sodium nitrate. Sodium sulfate and sodium chloride are particularly preferable from the viewpoints of being neutral salts and not promoting hydrolysis of the α-SF salt.

The inorganic potassium salt may be that which is ordinarily incorporated as a detergent component, and examples include potassium sulfate, potassium sulfite, potassium chloride, potassium bicarbonate and potassium nitrate. Potassium sulfate and potassium chloride are particularly preferable from the viewpoints of being neutral salts and not promoting hydrolysis of the α-SF salt.

The concentration of component (b) in the aqueous α-SF salt solution is such that the total concentration of sodium ions and potassium ions derived from the component (b) is within a range of less than 4.3 mol/kg, and can be determined in consideration of the α-SF salt concentration of the target aqueous α-SF salt solution. If the total concentration of sodium ions and potassium ions derived from the component (b) is equal to or greater than 4.3 mol/kg, the viscosity of the aqueous α-SF salt solution increases considerably due to salting out, thereby making procedures such as stirring and transfer difficult.

<Method for Producing Aqueous α-SF Salt Solution>

The method for producing an aqueous α-SF salt solution of the present invention consists of producing an aqueous α-SF salt solution by dissolving the solid component (a) in a solvent in the form of water under temperature conditions of 50° C. or higher while maintaining the solid component (a) and the component (b) under the conditions of (i) to (iii) below.

The aforementioned solid α-SF salt-containing product, for example, can be used as a supply source of the solid component (a). The component (b) contains an inorganic sodium salt and/or inorganic potassium salt contained in the solid α-SF salt-containing product and obtained by newly adding an inorganic sodium salt and/or inorganic potassium salt to a solvent.

Dissolution of the solid component (a) in water is (i): carried out while maintaining the concentration of component (a) at 35% by weight or less, and preferably carried out while maintaining the concentration of component (a) at 33% by weight or less, in the case the total concentration of sodium ions and potassium ions derived from component (b) is less than 0.55 mol/kg. If the total concentration of sodium ions and potassium ions derived from component (b) is less than 0.55 mol/kg, it becomes difficult to dissolve the α-SF salt, the amount of α-SF salt adhered to the production equipment increases or a considerable increase in viscosity of the aqueous α-SF salt solution occurs, thereby making procedures such as stirring or transfer difficult, if the concentration of component (a) exceeds 35% by weight.

Dissolution of the solid component (a) in water is (ii): carried out while maintaining the concentration of component (a) at 55% by weight or less, preferably carried out while maintaining the concentration of component (a) at 53% by weight or less, and more preferably carried out while maintaining the concentration of component (a) at 50% by weight or less in the case the total concentration of sodium ions and potassium ions derived from component (b) is 0.55 mol/kg to less than 1.8 mol/kg. If the total concentration of sodium ions and potassium ions derived from component (b) is 0.55 mol/kg to less than 1.8 mol/kg, it becomes difficult to dissolve the α-SF salt, the amount of α-SF salt adhered to the production equipment increases or a considerable increase in viscosity of the aqueous α-SF salt solution occurs, thereby making procedures such as stirring or transfer difficult, if the concentration of component (a) exceeds 55% by weight.

Dissolution of the solid component (a) in water is (iii): carried out while maintaining the concentration of component (a) within the range represented by the following formula (1) in the case the total concentration of sodium ions and potassium ions derived from component (b) is 1.8 mol/kg to less than 4.3 mol/kg:

$$y \leq -22x + 95 \quad (1)$$

(wherein, y represents the concentration of the component (a) (wt %), and x represents the total concentration of sodium ions and potassium ions derived from the component (b) (mol/kg)).

If the total concentration of sodium ions and potassium ions derived from component (b) in the aqueous α-SF salt solution is 1.8 mol/kg to less than 4.3 mol/kg, it becomes difficult to dissolve component (a) unless the above formula (1) is satisfied. In addition, if the total concentration of sodium ions and potassium ions derived from component (b) is 4.3 mol/kg or more, a considerable increase in viscosity of the aqueous α-SF salt solution occurs due to salting out, thereby making procedures such as stirring or transfer difficult.

The method used to dissolve the solid component (a) and the component (b) in water is required to maintain the conditions of (i) to (iii) described above, and an example of such a method consists of placing water used as solvent and the component (b) in a dissolving tank and dissolving the component (b) by stirring followed by adding the solid component (a) while maintaining the water at a prescribed temperature and dissolving by stirring. In addition, another method consists of placing water used as solvent in a dissolving tank, simultaneously adding the solid component (a) and the component (b) while stirring at a prescribed temperature, and then dissolving by stirring.

In addition, the solid component (a) and the component (b) may also be dissolved by incrementally adding water used as solvent thereof. For example, a portion of the entire volume of water (entire volume to be placed in dissolving tank) used as solvent may be placed in the dissolving tank as an initial solvent followed by adding and dissolving the solid component (a) and the component (b) in the initial solvent while maintaining the conditions of (i) to (iii) above (preliminary dissolution step). Next, the amount of water remaining after subtracting the volume of the initial solvent from the total amount of water to be placed in the dissolving tank is then placed in the dissolving tank. Subsequently, the amount of the solid component (a) and the component (b) remaining after subtracting the amounts of the solid component (a) and the component (b) used in the preliminary dissolution step from the total amount of the solid component (a) and the component (b) placed in the dissolving tank is added and dissolved while maintaining the conditions (i) to (iii) described above (primary dissolution step). At this time, the volume of the initial solvent is preferably 20% by weight or more, more preferably 30% by weight or more, even more preferably 40% by weight or more, and particularly preferably 60% by weight or more of the total volume placed in the dissolving tank. The procedure for dissolving the component (a) can be initiated smoothly by initiating production of the aqueous α-SF salt solution by using the initial solvent at 20% by weight or more of the total volume of solvent placed in the dissolving tank. If the volume of the initial solvent used is less than 20% by weight the total volume of solvent placed in the dissolving tank, it becomes difficult to dissolve the α-SF salt, the amount of α-SF salt adhered to the production equipment increases or a considerable increase in viscosity of the aqueous α-SF salt solution occurs, thereby making procedures such as stirring or transfer difficult.

The temperature when dissolving the solid component (a) in water is 50° C. or higher, preferably 55° C. or higher and more preferably 60 to 90° C. If the temperature is lower than 50° C., viscosity of the aqueous α-SF salt solution increases making procedures such as stirring and transfer difficult. If the temperature is excessively high, the water used as solvent may evaporate, thereby making it difficult to adjust the concentrations of each component. The component (a) can be favorably dissolved if the temperature is within the ranges described above.

The addition rate of the solid component (a) to water can be determined in consideration of the total concentration of sodium ions and potassium ions derived from the component (b). The addition rate of the solid component (a) to water is such that the relative addition rate of the solid component (a) to the solvent as represented by the following formula (2) is preferably $0.1\ h^{-1}$ to less than $10\ h^{-1}$, more preferably $0.3\ h^{-1}$ to less than $8\ h^{-1}$, and even more preferably $0.5\ h^{-1}$ to less than $5\ h^{-1}$. If the relative addition rate of the solid component (a) is less than $0.1\ h^{-1}$, productivity of the aqueous α-SF salt solution decreases, thereby making this undesirable. If the relative addition rate of the solid component (a) is $10\ h^{-1}$ or more, the concentration of the α-SF salt becomes partially high and an increase in the viscosity of the aqueous α-SF salt solution occurs, thereby making procedures such as stirring or transfer difficult.

Relative addition rate of solid component (a)=addition rate of solid component (a) (kg/h)/final amount of aqueous α-sulfo fatty acid alkyl ester salt solution (kg) (2)

As has been described above, the method for producing an aqueous α-SF salt solution of the present invention facilitates the dissolution of a solid α-SF salt in water and inhibits large increases in viscosity of an aqueous α-SF salt solution by dissolving the solid component (a) in water under temperature conditions of 50° C. or higher while maintaining the conditions of (i) to (ii) as previously described. Consequently, in addition to maintaining fluidity of the aqueous α-SF salt solution, adhesion of the α-SF salt to various production equipment can be prevented, and work adaptability is improved without impairing procedures such as stirring or transport.

In addition, since the solid component (a) is dissolved in water under temperature conditions of 50° C. or higher while maintaining the aforementioned condition (iii), the method for producing an aqueous α-SF salt solution of the present invention is able to improve work adaptability by preventing increases in viscosity of the aqueous α-SF salt solution caused by salting out.

The following provides a discussion of the mechanism of this effect of inhibiting increases in viscosity of an aqueous α-SF solution.

In the case the total concentration of sodium ions and potassium ions derived from the component (b) is less than 0.55 mol/kg and the α-SF salt concentration exceeds 35% by weight, the effect of adding sodium ions and potassium ions is inadequate, and viscosity increases rapidly due to the formation of hexagonal liquid crystals in the α-SF salt. Namely, the formation of hexagonal liquid crystals in the α-SF salt is thought to be prevented and increases in viscosity of an aqueous α-SF salt solution are inhibited by making the α-SF salt concentration 35% by weight or less.

In the case the α-SF salt concentration in the aqueous α-SF salt solution is greater than 35% by weight and 55% by weight or less and the total concentration of sodium ions and potassium ions is less than 0.55 mol/kg, hexagonal liquid crystals are thought to form in the α-SF salt. Under conditions causing the formation of hexagonal liquid crystals, the α-SF salt is arranged in a circular form with the alkyl chain on the inside, sulfonate groups serving as anions are located on the outside, and adjacent sulfonate groups repel each other. However, if sodium ions and/or potassium ions serving as cations are at a prescribed concentration (0.55 mol/kg or more to less than 1.8 mol/kg), the repulsion between adjacent sulfonate groups weakens, and the circular arrangement of the α-SF salt is no longer maintained, resulting in a parallel arrangement. Since this arrangement is that of lamellar liquid crystals, viscosity decreases considerably as compared with hexagonal liquid crystals. Namely, increases in viscosity of the aqueous α-SF salt solution are thought to be inhibited by preventing the formation of hexagonal liquid crystals in the α-SF salt or transforming α-SF salt in which hexagonal liquid crystals have been partially formed to lamellar liquid crystals in the production process of an aqueous α-SF salt solution.

In the case the total concentration of sodium ions and potassium ions derived from the component (b) is 1.8 mol/kg to less than 4.3 mol/kg, it becomes difficult to dissolve the α-SF salt and the α-SF salt is salted out corresponding to the concentrations of sodium ions and potassium ions derived from the component (b). Consequently, the viscosity of the aqueous α-SF salt solution increases considerably due to the salt out α-SF salt. Namely, increases in viscosity of aqueous α-SF salt solution are thought to be inhibited by maintaining solubility of the α-SF salt in the solvent.

The aqueous α-sulfo fatty acid ester salt solution of the present invention can be incorporated in a powdered detergent composition of textile products and a powdered detergent composition for tableware as spray-dried granules obtained by spray drying after having mixed with other components to form a slurry. Examples of components contained in these powdered detergent compositions include anionic surfactants such as α-SF salts, linear alkylbenzene sulfonates, α-olefin sulfonates, alkyl sulfates or soaps, nonionic surfactants such as alkylene oxide addition products of higher alcohols, builders such as zeolite, sodium sulfate or sodium sulfite and other inorganic builders, alkaline agents such as sodium carbonate or potassium carbonate, fluorescent agents, bleaches, bleach activators, enzymes, fragrances, softeners such as bentonite, cationic cellulose or powdered cellulose, and anti-redeposition agents such as carboxymethyl cellulose, hydroxypropyl methylcellulose or polyethylene glycol.

EXAMPLES

Although the following provides a detailed explanation of the present invention by listing examples thereof, the present invention is not limited to these examples. Furthermore, unless specifically indicated otherwise, the term "%" represents "% by weight", while the term "parts" represents "parts by weight".

(Raw Materials Used)
α-SF Salt-Containing Flakes
<Production of α-SF Salt-Containing Paste>

330 kg of a mixture of fatty acid methyl esters (mixture obtained by premixing methyl palmitate (Lion, trade name: Pastell M-16) and methyl stearate (Lion, trade name: Pastell M-180) to a weight ratio of 9:1) were placed in a reaction apparatus equipped with a stirrer and having a capacity of 1 kL. 5 parts of a coloring inhibitor in the form of anhydrous sodium sulfate were added to 100 parts of the fatty acid methyl ester mixture while stirring the fatty acid methyl ester mixture in the reaction apparatus. 110 kg (1.2 moles based on the fatty acid methyl ester mixture) of $SO_3$ gas (sulfonating gas) diluted to 4% by weight with nitrogen gas were blown at constant rate into the reaction apparatus over the course of 3 hours while bubbling at a reaction temperature of 80° C. while continuing to stir the reaction apparatus. Subsequently, aging was carried out for 30 minutes while holding at 80° C.

14 kg of a lower alcohol in the form of methanol was supplied to the reaction apparatus to carry out esterification of the sulfonation product. The esterification product was obtained by using an esterification temperature of 80° C. and an aging time was 30 minutes.

The esterification product was removed from the reaction apparatus and continuously neutralized by adding aqueous sodium hydroxide solution using a line mixer to obtain an α-SF salt-containing neutralization product.

Next, the resulting α-SF salt-containing neutralization product was injected into a bleaching agent mixing line and 1 to 2 parts were supplied based on 100 parts of AI in terms of the pure content of 35% aqueous hydrogen peroxide followed by mixing and bleaching while holding at 80° C. to obtain an α-SF salt-containing paste containing an α-SF salt in the form of a sodium salt of an α-sulfo methyl ester (MES). Here, "AI" indicates the α-SF salt serving as the active ingredient. Normally, an α-SF salt-containing paste contains disalts of α-sulfo fatty acids such as disalts of sodium α-sulfo fatty acids (di-Na salts) and by-products such as inorganic sulfates. The color tone of the resulting α-SF salt-containing paste was 30. Color tone was measured by preparing a 5% ethanol solution of the resulting α-SF salt-containing paste and measuring with a klett photometric colorimeter using an optical path length of 40 mm and a No. 42 blue filter.

<Concentration of α-SF Salt-Containing Paste>

The resulting α-SF salt-containing paste was concentrated under conditions consisting of an inner wall heating temperature (temperature of heat-conducting surface) of 135° C. and a degree of vacuum (pressure within the treatment unit) of 0.007 to 0.014 MPa by introducing at the rate of 35 kg/h into a thin film vacuum evaporator rotating at 1,060 rpm at an impeller tip speed of about 11 m/sec (surface area of heat conducting surface: 0.5 $m^2$, inner diameter of cylindrical treatment unit: 205 mm, clearance between heat-conducting surface and impeller tip as means for peeling the paste: 3 mm, trade name: Exeva, Kobelco Eco-Solutions) to obtain a concentrate of the α-SF salt-containing paste.

The temperature of the resulting α-SF salt-containing paste concentrate was 115° C. and the moisture content was 2.4%. Furthermore, the moisture content was measured using a Karl Fischer moisture meter (Kyoto Electronics Manufacturing, Model MKC-210, Method 2, stirring speed: 4). The sample size was about 0.05 g.

The composition of the resulting α-SF salt-containing paste concentrate was measured according to the method described below.

<<Measurement of Total Concentration of MES and di-Na Salt>>

0.3 g of the α-SF salt-containing paste concentrate were accurately weighed out in a 200 mL volumetric flask and dissolved ultrasonically by adding ion exchange water (distilled water) to the marked line. After dissolving, the solution was cooled to about 25° C., 5 mL of the solution were transferred to a titration bottle with a Hall pipette followed by the addition of 25 mL of MB (methylene blue) indicator and 15 mL of chloroform, and further adding 5 mL of 0.004 mol/L benzethonium chloride solution and titrating with 0.002 mol/L sodium alkylbenzene sulfonate solution. Titration was carried out sealing the titration bottle, shaking vigorously and allowing to stand undisturbed after each addition, and defining the endpoint as the point where both layers become the same color when viewed using a white board as a background. A blank test (same test as described above with the exception of not using bleached paste) was similarly carried out, and the total concentration of MES and di-Na salt was calculated from the difference in the titrated amounts.

<<Measurement of di-Na Salt Concentration>>

Ratio of di-Na Salt in Total Concentration of MES and di-Na Salt 0.02, 0.05 and 0.1 g of a di-Na salt standard were accurately weight out in 200 mL volumetric flasks and dissolved ultrasonically by adding about 50 mL of water and about 50 mL of ethanol. After dissolving, the solutions were cooled to about 25° C., methanol was accurately added to the marked line and these were used as standard solutions.

About 2 mL of the standard solutions were filtered using a 0.45 μm Chromatodisk filter, followed by analyzing by high-performance liquid chromatography under the conditions described below and preparing a calibration curve from the peak areas.

High-Performance Liquid Chromatography Analysis Conditions
  Apparatus: LC-6A (Shimadzu)
  Column: Nucleosil 5SB (GL Science)
  Column temperature: 40° C.
  Detector: Differential refractive index detector RID-6A (Shimadzu)
  Mobile phase: $H_2O/CH_3OH$ ratio of 0.7% sodium perchlorate solution=¼ (volume ratio)
  Flow rate: 1.0 mL/min
  Injection volume: 100 μL Next, 1.5 g of the α-SF salt-containing paste concentrate were accurately weighed out in a 200 mL volumetric flask and dissolved ultrasonically by adding about 50 mL of water and about 50 mL of ethanol. After dissolving, the solution was cooled to about 25° C., methanol was accurately added to the marked line, and this was used as a test solution. After filtering about 2 mL of the test solution with a 0.45 μm Chromatodisk filter, the test solution was analyzed by high-performance liquid chromatography under the same measurement conditions as described above followed by determining the di-Na salt concentration in the sample solution using the calibration curve prepared as previously described.

The ratio of MES and di-Na salt (wt %) in the total concentration of MES and di-Na salt obtained in the aforementioned section entitled "<<Measurement of Total Concentration of MES and di-Na Salt>>" was calculated from the determined di-Na salt concentration and the total concentration of MES and di-Na salt determined in the aforementioned section entitled "<<Measurement of Total Concentration of MES and di-Na Salt>>".

<<Measurement of Sodium Sulfate Concentration and Methyl Sulfate Concentration>>

0.02, 0.04, 0.1 and 0.2 g of sodium sulfate and methyl sulfate standard were accurately weighed out in 200 mL volumetric flasks, and dissolved ultrasonically by adding ion exchange water (distilled water) to the marked line. After dissolving, the solutions were cooled to about 25° C. and used as standard solutions. After filtering about 2 mL of the standard solutions using a 0.45 μm Chromatodisk filter, the standard solutions were analyzed by ion chromatography under the conditions indicated below to prepare calibration curves from the peak areas of the methyl sulfate and sodium sulfate standard solutions.

Ion Chromatography Analysis Conditions
  Apparatus: DX-500 (Nippon Dionex)
  Detector: Electrical conductivity detector CD-20 (Nippon Dionex)
  Pump: IP-25 (Nippon Dionex)
  Oven: LC-25 (Nippon Dionex)
  Integrator: C-R6A (Shimadzu)
  Separation column: AS-12A (Nippon Dionex)
  Guard column: AG-12A (Nippon Dionex)
  Eluate: 2.5 mM Na $CO_2$/2.5 mM NaOH/5 vol % aqueous acetonitrile solution
  Eluate flow rate: 1.3 mL/min
  Regeneration liquid: Pure water
  Column temperature: 30° C.
  Loop volume: 25 μL Next, 0.3 g of α-SF salt-containing paste concentrate were accurately weighed out into a 200 mL volumetric flask and dissolved ultrasonically by adding ion exchange water (distilled water) to the marked line. After dissolving, the solution was cooled to about 25° C. and used as a test solution. About 2 mL of the test solution were filtered using a 0.45 μm Chromatodisk filter followed by analyzing by ion chromatography under the same measurement conditions as described above, the methyl sulfate concentration and sodium sulfate concentration in the test solution were determined using the calibration curve prepared as described above followed by calculating the methyl sulfate concentration and sodium sulfate concentration (wt %) in the sample.

<<Measurement of Methanol Concentration and Unreacted Methyl Ester Concentration>>

Gas chromatography was carried out in accordance with ordinary methods, and methanol concentration and unreacted methyl ester concentration were calculated from a comparison between the peak areas of test solutions and standard solutions of methanol and unreacted methyl ester.

The composition of the concentrate obtained in the aforementioned measurements is as indicated below.

| | |
|---|---|
| MES | 85.4% |
| Moisture | 2.4% |
| Methyl sulfate | 6.1% |
| Sodium sulfate | 2.5% |
| di-Na salt | 3.6% |
| Methanol | Trace (residue observed) |
| Unreacted methyl ester | Trace (residue observed) |
| Other trace components | Trace (residue observed) |
| Total | 100.0% |

<Flaking of Concentrate>

The resulting α-SF salt-containing paste concentrate was continuously supplied to a double-belt-type belt cooler (NR3-Lo.cooler) manufactured by Nippon Belting adjusted to a clearance between the loading pulleys of 2 mm at the rate of 222 kg/h and cooled. At this time, the belt traveling speeds were set to the values indicated below, and the cooling water flow rates were set to 1500 L/h for the upper belt (cooling by flowing downward in the manner of countercurrent over the back of the belt) and 1800 L/h for the lower belt (cooling by spraying onto the back of the belt), and the cooling water supply temperature was 20° C. A surfactant-containing sheet at 25° C. obtained by being discharged from the cooling belts was crushed at a rotating speed of 200 rpm with an ancillary crusher installed in the vicinity of the discharge pulleys to obtain α-SF salt-containing flakes containing solid α-SF salt.

<<Specifications of Double Belt-Type Belt Cooler>>
  Distance between pulley cores: (upper/lower) [mm]: 3270/3630
  Upper belt specifications (L×W×T) [mm]: 8440×650×0.8
  Lower belt specifications: (L×W×T) [mm]: 8440×650×0.8
  Belt speed [m/min]: 6
  Effective cooling length [m]: 3.1
  Effective cooling width [m]: 0.47

α-SF Salt-Containing Pellets

α-SF salt-containing flakes were continuously loaded at a processing speed of 80 kg/h into the raw material hopper of an Extrudomix (Hosokawa Micron, Model EM-6, primary shaft rotating speed: 70 rpm) equipped with an intermediate orifice (first intermediate orifice diameter: 46 mm, second intermediate orifice diameter: 4.5 mm) followed by kneading and extruding to obtain an α-SF salt-containing product in the form of noodles having a diameter of φ0.8 mm (temperature: 60° C.) Furthermore, the water jacket inlet temperature of the Extrudomix at this time was 30° C. After cooling this noodle-shaped α-SF salt-containing product to 30° C. at room temperature, it was crushed by loading into a speed mill (Okada Seiko, Model ND-10, blade rotating speed: 840 rpm, screen diameter: ϕ2 mm) at a processing speed of 1 kg/min to obtain a solid α-SF salt-containing product in the form of α-SF salt-containing pellets having an average long axis (pellet length) of 2.4 mm that contained solid α-SF salt.

α-SF Salt-Containing Powder

α-SF salt-containing flakes were introduced into a two-stage Fitz mill arranged in series (Hosokawa Micron, Model DKA-3, first stage screen diameter: ϕ8 mm, second stage screen diameter: ϕ3.5 mm, blade rotating speed: first stage 4700 rpm, second stage: 2820 rpm) together with dehumidified cooling air at 15° C. (dew point: −5° C., blowing rate: 6 Nm$^3$/min) followed by crushing at a processing speed of 200 kg/h to obtain α-SF salt-containing power having a mean particle diameter of 500 μm that contained solid α-SF salt. Furthermore, "Nm$^3$" represents "m$^3$ (standard state)".

Aqueous hydrogen peroxide: analytical grade, aqueous solution containing 35% hydrogen peroxide (Junsei Chemical)

Sodium sulfate: Neutral anhydrous sodium sulfate A0 (Shikoku Chemicals)

Potassium sulfate: Analytical grade potassium sulfate (Takasugi Pharmaceutical)

Sodium chloride: Analytical grade sodium chloride (Kanto Chemical)

Potassium chloride: Industrial grade potassium chloride (Takasugi Pharmaceutical)

Sodium sulfite: Anhydrous sodium sulfite (Kamisu Chemical)

Potassium sulfite: Potassium sulfite (Daito Chemical)

Potassium nitrate: Analytical grade potassium nitrate (Kanto Chemical)

Potassium bicarbonate: Analytical grade potassium bicarbonate (Kanto Chemical)

(Measurement Methods and Evaluation Methods)

<Measurement of Mean Particle Diameter>

The mean particle diameter of the α-SF salt-containing powder was measured according to the method described below.

The α-SF salt-containing powder targeted for measurement (sample) was sized using nine sizes of sieves and holding dishes having mesh sizes of 1680 μm, 1410 μm, 1190 μm, 1000 μm, 710 μm, 500 μm, 350 μm, 250 μm and 149 μm. Sizing was carried out by stacking the sieves on the holding dish in order moving from the sieve having the smallest mesh size to the sieve having the largest mesh size, placing spray-dried granules of the sample on the highest sieve having a mesh size of 1680 μm at the rate of 100 g/test, covering the sieve, installing on a Ro-Tap sieve shaker (Iida Seisakusho, tapping rate: 156 times/min, rolling rate: 290 time/min) and shaking for 10 minutes under atmospheric conditions of a temperature of 25° C. and relative humidity of 40%, followed by recovering the sample remaining on each sieve and holding plate for each mesh size and measuring the weight of the sample. When the weight frequency of the holding dish and each sieve is integrated, mean particle diameter (50 wt %) was determined according to the following equation (3) by defining the mesh size of the first sieve for which the integrated weight frequency is 50% or more as aμm, the mesh size of a sieve having an integrated weight frequency larger than that of aμm as bμm, defining integration of the weight frequency from the holding dish to the sieve of aμm as c %, and defining the weight frequency of the sieve of aμm as d %.

[Equation 1]

Mean particle diameter (50 wt % particle diameter)=
$10^{[50-\{c-d/(\log b - \log a) \times \log b\}]/\{d/(\log b - \log a)\}}$ (3)

<Measurement of Aqueous α-SF Salt Solution Viscosity>

800 g of an aqueous α-SF salt solution were filled into a cylindrical stainless steel container having a depth of 115 mm and diameter of 110 mm, and viscosity was measured under the conditions indicated below using a Model B8H viscometer manufactured by Tokyo Keiki. Furthermore, values obtained 10 seconds after starting rotation of the rotor were used as measured values.

<<Measurement Temperature Conditions>>

Measured at 55° C. when temperature at time of production of aqueous α-SF salt solution was 50° C. to less than 60° C.

Measured at 65° C. when temperature at time of production of aqueous α-SF salt solution was 60° C. to less than 70° C.

Measured at 75° C. when temperature at time of production of aqueous α-SF salt solution was 70° C. to less than 80° C.

<<Measurement Conditions>>

Measured at 20 rpm with No. 4 rotor when viscosity range of aqueous α-SF salt solution was less than 10 Pa·s Measured at 20 rpm with No. 5 rotor when viscosity range of aqueous α-SF salt solution was 10 Pa·s to less than 20 Pa·s Measured at 20 rpm with No. 6 rotor when viscosity range of aqueous α-SF salt solution was 20 Pa·s to less than 50 Pa·s <Measurement of Maximum Required Stirring Power>

Required stirring power was measured in the manner described below using the dissolving tank equipped with a stirrer shown in FIG. 1 (to be simply referred to as the dissolving tank) 10.

Figure 1:
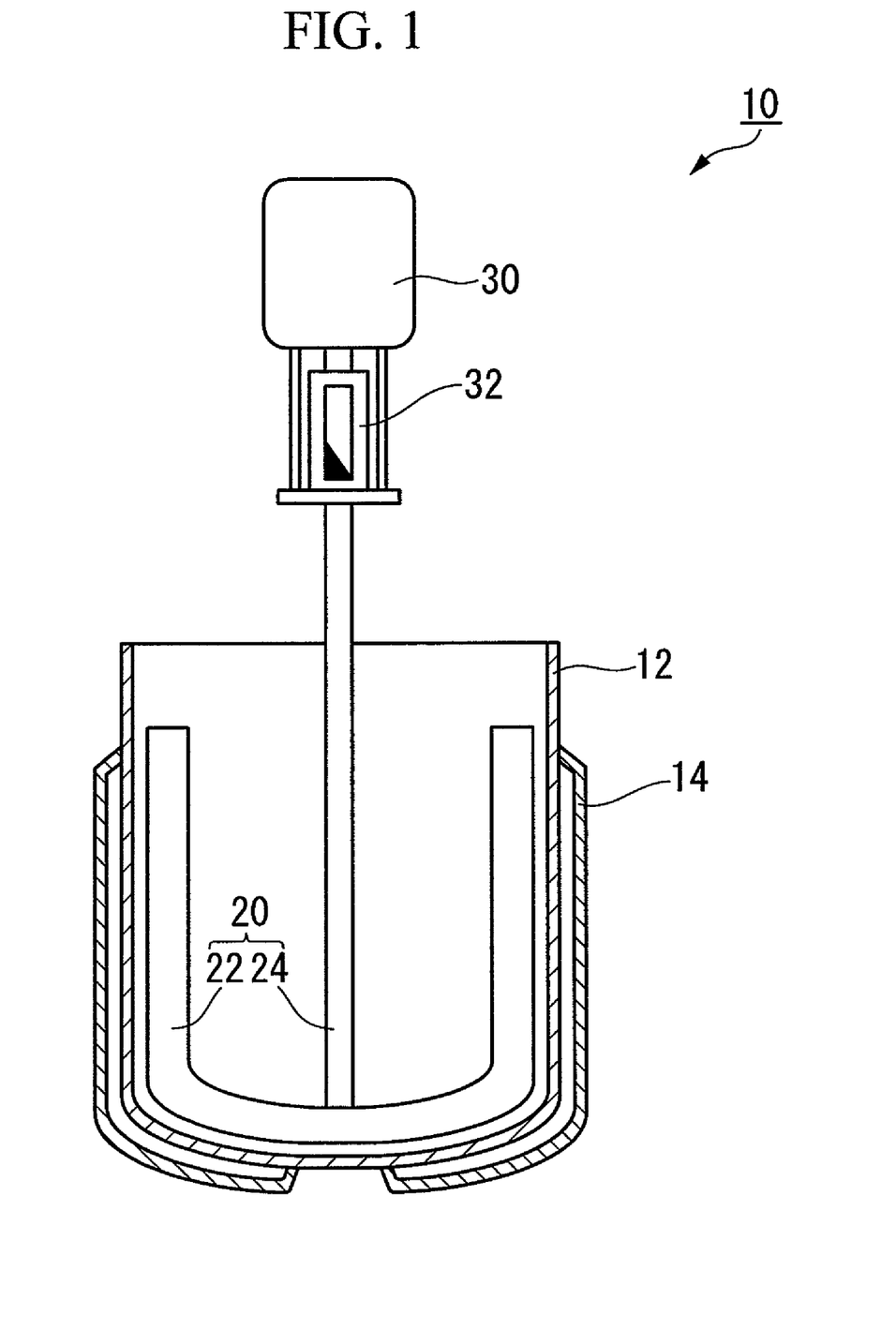
FIG. 1 is a cross-sectional view for explaining a dissolving tank used in the examples.

FIG. 1 is a cross-sectional view of the dissolving tank 10. The dissolving tank 10 has a body 12, a jacket 14 provided around the outer periphery of the body 12, and a stirring unit 20. The stirring unit 20 is composed of an anchor-type stirring impeller 22 and a stirring shaft 24, and the stirring shaft 24 is connected to a drive unit 30 through a torque meter 32. The dissolving tank 10 has a structure that enables the inside of the body 12 to be adjusted to an arbitrary temperature by allowing a heating medium to flow through the jacket 14. A rotary torque meter (Model SS-50 Yamazaki-type rotary torque meter, Yamazaki Seiki) was used for the torque meter 32.

Maximum required stirring power was measured by measuring the maximum rotary torque during production of the aqueous α-SF salt solution with the torque meter 32. The maximum required stirring power was calculated from the maximum rotary torque and the rotating speed at that time according to the following equation (4).

$$P = T \times 2\pi \times n \quad (4)$$

P: Maximum required stirring power [W]
T: Maximum rotary torque [J]
n: Rotating speed [rps]

<Evaluation of Adhesion to Stirring Impeller and Shaft>

After completing the procedure for producing an aqueous α-SF salt solution, adhesion of solid α-SF salt to the stirring impeller 22 and the stirring shaft 24 of the dissolving tank 10 shown in FIG. 1 was visually observed and evaluated according to the evaluation criteria indicated below. Here, a solid refers to a state that remains in the form of flakes, pellets or powder without dissolving in water.

<<Evaluation Criteria>>

A: Hardly any adhesion of solid α-SF salt
B: Slight adhesion of solid α-SF salt observed
C: Large amount of adhesion of solid α-SF salt observed <Overall Evaluation>

An overall evaluation of the aqueous α-SF salt solution obtained in Examples 1 to 56 and Comparative Examples 1 to 13 was carried out in accordance with the following evaluation criteria based on maximum required stirring power, viscosity and adhesion evaluation results. An overall evaluation of A, B or C was determined to indicate a level of quality suitable for actual production.

<<Evaluation Criteria>>

A: Solution satisfying all requirements that maximum required stirring power of 20 W or less, viscosity of 10 Pa·s or less and adhesion evaluated as grade A B: Solution satisfying all requirements that maximum required stirring power of greater than 20 W to 40 W or less, viscosity of 10 Pa·s or less and adhesion evaluated as grade A C: Solutions other than those having an overall evaluation of D, satisfying either maximum required stirring power of greater than 40 W to 55 W or less or viscosity of greater than 10 Pa·s to 25 Pa·s or less, and adhesion evaluated as grade A or B D: Solutions satisfying any one of maximum required stirring power of greater than 55 W, viscosity of greater than 25 Pa·s and adhesion evaluated as grade C Examples 1 to 47 and 50 to 53 and Comparative Examples 1 to 11

25 kg of the aqueous α-SF salt solution of each example was produced in accordance with the compositions shown in Tables 1 to 8 according to the method indicated below. First, steam at 100° C. was passed through the jacket 14 of the dissolving tank 10 shown in FIG. 1, and water at the temperatures shown in Tables 1 to 8 was added so as to ultimately yield the compositions of the aqueous α-SF salt solutions shown in Tables 1 to 8. Continuing, rotation of the stirring unit 20 was started at a rotating speed of 103 rpm followed by the simultaneous addition of the entire amount of inorganic sodium salt and/or inorganic potassium salt. After continuing to stir for 2 minutes, a solid α-SF salt-containing product was then added at the relative addition rates shown in Tables 1 to 8. Following addition, stirring was continued for an additional 15 minutes to obtain an aqueous α-SF salt solution. The amount of steam fed to the jacket 14 was controlled so as to be able to maintain the temperature of the aqueous α-SF salt solution within the temperature ranges shown in Tables 1 to 8 during the course of production. Those aqueous α-SF salt solutions produced according to the production method described above are indicated with an "a" in the row entitled "Addition Order" of Preparation Conditions in Tables 1 to 8.

Example 48

25 kg of the aqueous α-SF salt solution of each example was produced in accordance with the composition shown in Table 8 according to the method indicated below. First, steam at 100° C. was passed through the jacket 14 of the dissolving tank 10 shown in FIG. 1, and water at the temperature shown in Table 8 was added to the dissolving tank 10 as an initial solvent that was equivalent to 55% of the total amount added. Continuing, rotation of the stirring unit 20 was started at a rotating speed of 103 rpm followed by the simultaneous addition of the entire amount of inorganic sodium salt and/or inorganic potassium salt. After continuing to stir for 2 minutes, a solid α-SF salt-containing product was then added at the relative addition rate shown in Table 8 (preliminary dissolving step). Next, the remainder of the water at the temperature indicated in Table 8 (equivalent to 45% of the total amount of water added) was added all at once and stirring was continued to an additional 15 minutes after addition to obtain an aqueous α-SF salt solution (primary dissolving step). The amount of steam fed to the jacket 14 was controlled so as to be able to maintain the temperature of the aqueous α-SF salt solution within the temperature range shown in Table 8 during the course of production. The aqueous α-SF salt solution produced according to the production method described above is indicated with a "b" in the row entitled "Addition Order" of Preparation Conditions in Table 8.

Example 49

25 kg of an aqueous α-SF salt solution was obtained in the same manner as Example 48 in accordance with the composition shown in Table 8 with the exception of making the amount of initial solvent added equivalent to 60% of the total amount of solvent added. The aqueous α-SF salt solution produced according to the production method described above is indicated with a "b" in the row entitled "Addition Order" of Preparation Conditions in Table 8.

Example 54

25 kg of an aqueous α-SF salt solution were obtained in the same manner as Example 1 in accordance with the composition shown in Table 8 with the exception of simultaneously adding sodium sulfate and solid α-SF salt-containing product. At this time, the relative addition rate of the sodium sulfate was 0.20 h$^{-1}$, and the relative addition rate of the solid α-SF salt-containing product was 1.50 h$^{-1}$. The aqueous α-SF salt solution produced according to the production method described above is indicated with a "c" in the row entitled "Addition Order" of Preparation Conditions in Table 8.

Example 55

25 kg of an aqueous α-SF salt solution having an MES concentration of 48.0% and a concentration of sodium ions derived from an inorganic salt of 0.8 mol/kg were produced in accordance with the composition shown in Table 8 according to the method indicated below. First, steam at 100° C. was passed through the jacket 14 of the dissolving tank 10 shown in FIG. 1, and water at the temperature shown in Table 8 was added so as to ultimately yield the aqueous solution composition shown in Table 8. Continuing, rotation of the stirring unit 20 was started at a rotating speed of 103 rpm, the solid α-SF salt-containing product was added at a relative addition rate of 1.50 h$^{-1}$, and addition of the solid α-SF salt-containing product was discontinued when the MES concentration reached 30%. The concentration of sodium ions derived from an inorganic salt at this time was 0.11 mol/kg. Next, an equivalent of 4.4% of sodium sulfate was added all at once, the remainder of the solid α-SF salt-containing product was added at a relative addition rate of 1.50 h$^{-1}$ 2 minutes after adding the sodium sulfate, and stirring was continued for an additional 15 minutes after adding the solid α-SF salt-containing product to obtain an aqueous α-SF salt solution. The aqueous α-SF salt solution produced according to the production method described above is indicated with a "d" in the row entitled "Addition Order" of Preparation Conditions in Table 8.

Example 56

25 kg of an aqueous α-SF salt solution having an MES concentration of 43.2% and a concentration of sodium ions derived from an inorganic salt of 1.1 mol/kg was produced in accordance with the composition shown in Table 8 using an amount of water equivalent to 20% of the total amount of water added as an initial solvent according to the method indicated below. First, steam at 100° C. was passed through the jacket 14 of the dissolving tank 10 shown in FIG. 1, and water at the temperature shown in Table 8 was added to the dissolving tank 10 as an initial solvent that was equivalent to 20% of the total amount added. Continuing, rotation of the stirring unit 20 was started at a rotating speed of 103 rpm followed by the simultaneous addition of sodium sulfate at 20% of the total amount added. After continuing to stir for 2 minutes, a solid α-SF salt-containing product was added at 20% of the total amount added at the relative addition rate shown in Table 8. Next, the remainder of the water at the temperature indicated in Table 8 (80% of the total amount added) was added all at once, and after continuing to stir for 2 minutes, the remainder of the sodium sulfate (80% of total amount added) was further added all at once. After stirring for 2 minutes, the remainder of the solid α-SF salt-containing product (80% of the total amount added) was added at the relative addition rate shown in Table 8, and stirring was continued for an additional 15 minutes after addition to obtain an aqueous α-SF salt solution. The aqueous α-SF salt solution produced according to the production method described above is indicated with an "e" in the row entitled "Addition Order" of Preparation Conditions in Table 8.

Comparative Example 12

25 kg of an aqueous α-SF salt solution having an MES concentration of 43.2% and a concentration of sodium ions derived from an inorganic salt of 1.1 mol/kg was attempted to be produced in accordance with the composition shown in Table 9 according to the method indicated below. First, steam at 100° C. was passed through the jacket 14 of the dissolving tank 10 shown in FIG. 1, and water at the temperature shown in Table 9 was added so as to ultimately yield the composition of the aqueous α-SF salt solution indicated in Table 9. Continuing, rotation of the stirring unit 20 was started at a rotating speed of 103 rpm, and sodium sulfate equivalent to 1.7% of the total final composition was added all at once. After stirring for 2 minutes, a solid α-SF salt-containing product was added at the relative addition rate shown in Table 9. The viscosity of the aqueous solution increased when the MES concentration reached 38.4% (concentration of sodium ions derived from inorganic salt: 0.44 mol/kg), and production was discontinued since it became difficult to drive the stirring unit 20. Accordingly, an aqueous α-SF salt solution having an MES concentration of 43.2% and a concentration of sodium ions derived from an inorganic salt of 1.1 mol/kg was unable to be obtained. The aqueous α-SF salt solution produced according to the production method described above is indicated with an "f" in the row entitled "Addition Order" of Preparation Conditions in Table 9.

Comparative Example 13

25 kg of an aqueous α-SF salt solution having an MES concentration of 48.0% and a concentration of sodium ions derived from an inorganic salt of 0.8 mol/kg was attempted to be produced in accordance with the composition shown in Table 9 according to the method indicated below. First, steam at 100° C. was passed through the jacket 14 of the dissolving tank 10 shown in FIG. 1, and water at the temperature shown in Table 9 was added so as to ultimately yield the aqueous solution composition indicated in Table 9. Continuing, rotation of the stirring unit 20 was started at a rotating speed of 103 rpm, and a solid α-SF salt-containing product was added at a relative addition rate of 1.50 h$^{-1}$. Sodium sulfate was added at a relative addition rate of 0.22 h$^{-1}$ when the MES concentration reached 30%, and sodium sulfate and the solid α-SF salt-containing product were added simultaneously starting at this time. However, the viscosity of the aqueous solution increased when the MES concentration reached 38.4% (concentration of sodium ions derived from inorganic salt: 0.52 mol/kg), and production was discontinued since it became difficult to drive the stirring unit 20. Accordingly, an aqueous α-SF salt solution having an MES concentration of 48.0% and a concentration of sodium ions derived from an inorganic salt of 0.8 mol/kg was unable to be obtained. The aqueous α-SF salt solution produced according to the production method described above is indicated with a "g" in the row entitled "Addition Order" of Preparation Conditions in Table 9.

Formulation Examples 1 to 3

(Slurry Preparation Step)

Figure 3:
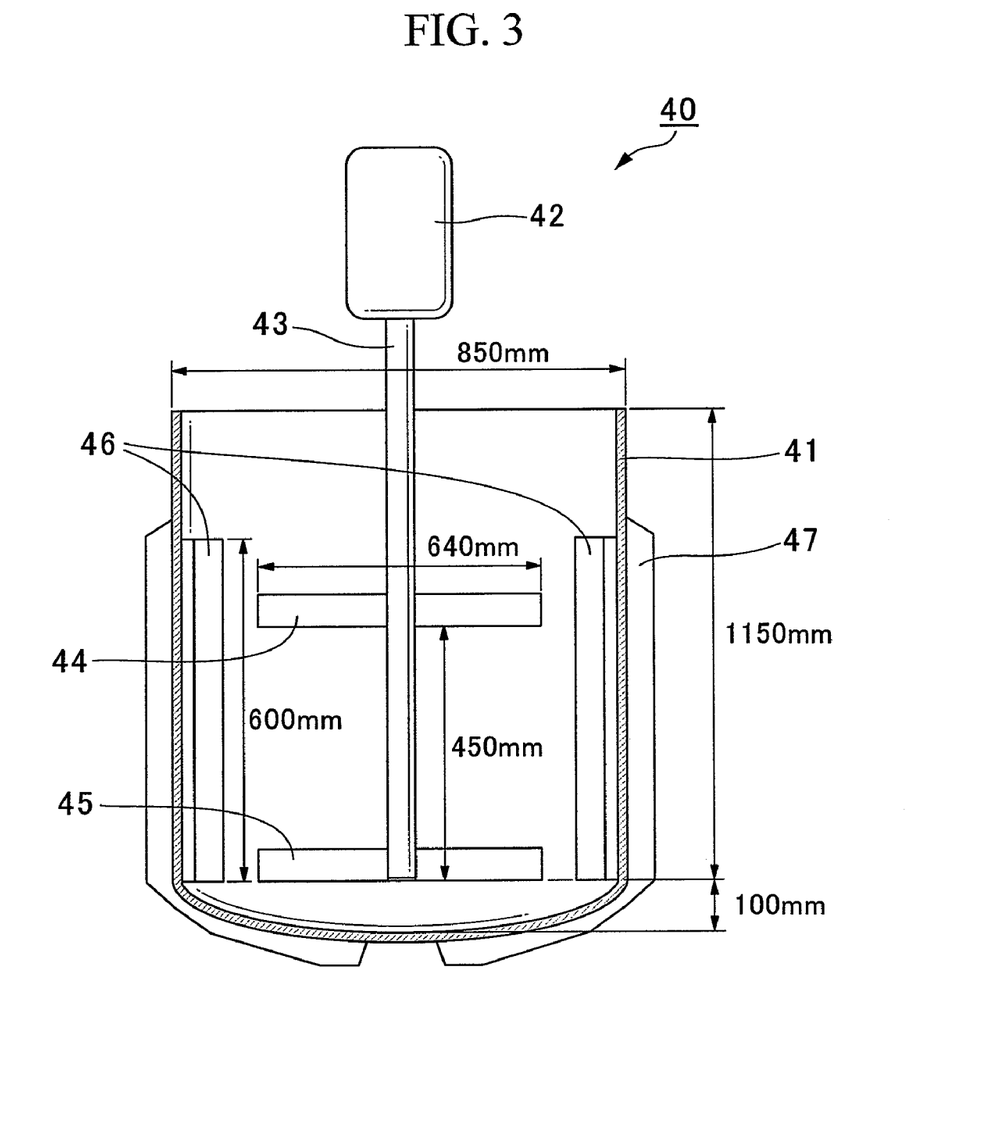
FIG. 3 is a cross-sectional view for explaining a dissolving tank used in a slurry preparation step of Formulation Examples 1 to 4.

FIG. 3 is a cross-sectional view of a dissolving tank 40 used in the slurry preparation step. The dissolving tank 40 has a structure that allows a heating medium to flow through a jacket 47 to adjust the inside of a mixing vessel 41 to an arbitrary temperature.

Water at 25° C. was added to the mixing vessel 41 equipped with two stages of inclined paddle impellers 44 and 45 inclined at an angle of 45° (impeller length: 640 mm, impeller width: 65 mm) and two baffle plates 46 (length: 600 mm, width: 50 mm, clearance with wall surface: 30 mm) and having an effective capacity of 700 L (see FIG. 3), the paddle impellers 44 and 45 were connected to a drive unit 42 and a stirring shaft 43 and rotated at 120 rpm (stirring was continued until completion of mixing) while adding sodium hydroxide, and after dissolving in the water, the solution was neutralized by adding LAS-H to form LAS-Na (LAS-Na in Table 10 indicates the amount neutralized and formed by mixing LAS-H and sodium hydroxide; ratio of amount of LAS-Na formed to amount of sodium hydroxide to amount of LAS-H added=10.00:1.25:9.36 (weight ratio)). Subsequently, builders were added in the order of sodium polyacrylate, sodium sulfate, sodium tripolyphosphate (STPP) and sodium carbonate. Finally, the α-SF-Na obtained in Examples 13, 16 and 30 were added, steam at a pressure of 0.1 MPa (gauge pressure) or cold water at 8° C. was passed through the jacket of the mixing tank while continuing to stir, the temperature was adjusted to the slurry temperature shown in Table 10, and stirring was continued for 1 hour at that temperature. 600 kg of a slurry having a moisture content of 42% was prepared in this manner.

Furthermore, the amount of sodium sulfate added was adjusted to the compositions of Formulation Examples 1 to 3 in Table 10 (using the α-SF Na slurries of Examples 13, 16 and 30, respectively) as the compositions after spray drying based on the total amount carried over from the respectively used α-SF Na slurries.

(Spray Drying Step)

Subsequently, the slurry was fed and sprayed from the top of a counter-flow type drying tower having a tower diameter of 2.0 m, an effective length of 5.6 m and a capacity of 400 kg/hr using a pressurized nozzle to obtain spray-dried granules having the moisture content shown in Table 10. A nozzle similar to that described in Example 2 of Japanese Unexamined Patent Application, First Publication No. H9-75786 was used for the nozzle, and spraying was carried out at a spraying pressure of 2 to 3.5 MPa. The hot air temperature in the drying tower at this time was adjusted to a range of 270 to 400° so that the spray-dried granules reached the moisture content shown in Table 10. The exhaust rate was 240 m³/min, and the properties of the resulting spray-dried granules are shown in Table 10.

Formulation Example 4

(Slurry Preparation Step)

A slurry was prepared in the same manner as Formulation Examples 1 to 3 with the exception of simultaneously adding a fluorescent agent with the sodium hydroxide, and adding builders in the order of sodium silicate, sodium polyacrylate, sodium acrylate/maleate copolymer, zeolite, sodium sulfate, sodium sulfite, STPP, potassium carbonate and sodium carbonate followed by adding a soap and finally adding the α-SF-Na obtained in Example 13.

Furthermore, the amount of sodium sulfate added was adjusted to the composition of Formulation Examples 4 in Table 11 as the composition after spray drying based on the total amount carried over from the α-SF Na slurry used.

(Spray Drying Step)

Spray-dried granules having the moisture content shown in Table 11 were subsequently obtained in the same manner as Formulation Examples 1 to 3. The properties of the resulting spray-dried granules are shown in Table 11.

The raw materials used in Formulation Examples 1 to 4 are indicated below.

LAS-H: Linear alkylbenzene sulfonate (Lion, LIPON LH-200) (AV value (number of mg of potassium hydroxide required to neutralize 1 g of LAS-H)=180.0)

Sodium hydroxide: Flaked caustic soda (Tsurumi Soda)

STPP: Sodium tripolyphosphate (Taiyo Kagaku)

Sodium silicate: S50° Sodium Silicate No. 1 (Nippon Chemical Industrial) ($SiO_2/Na_2O$ molar ratio=2.15)

Sodium polyacrylate: Aqualic DL-453 (Nippon Shokubai) (aqueous solution having purity of 35% by weight)

Sodium acrylate/maleate copolymer: Aqualic TL-400 (Nippon Shokubai) (aqueous solution having purity of 40% by weight)

Zeolite: A-Type Zeolite (purity: 47.5% by weight) (Nippon Chemical Industrial)

Sodium carbonate: Granular ash (Soda Ash Japan)

Potassium carbonate: Potassium carbonate (powder) (Asahi Glass)

Sodium sulfite: Anhydrous sodium sulfite (Kamisu Chemical)

Sodium sulfate: Neutral anhydrous sodium sulfate AO (Shikoku Chemicals)

Soap: Sodium fatty acid salt having 12 to 18 carbon atoms (purity: 67% by weight, titer: 40 to 45° C., molecular weight: 289)

Fluorescent agent: Tinopal CBS-X (Ciba Japan)

TABLE 1

| | | Examples | | | | | | | | | |
|---|---|---|---|---|---|---|---|---|---|---|---|
| | | 1 | 2 | 3 | 4 | 5 | 6 | 7 | 8 | 9 | 10 |
| Form of solid α-SF salt-containing product | | Flakes | Flakes | Flakes | Flakes | Flakes | Flakes | Flakes | Flakes | Flakes | Flakes |
| Composition | MES [wt %] | 28.8 | 28.8 | 33.6 | 33.6 | 28.8 | 28.8 | 33.6 | 33.6 | 38.4 | 38.4 |
| | di-Na salt [wt %] | 1.2 | 1.2 | 1.1 | 1.1 | 1.2 | 1.2 | 1.4 | 1.4 | 1.6 | 1.6 |
| | Sodium sulfate [wt %] | 0.8* | 3.9 | 0.9* | 3.9 | 5.7 | 10.7 | 5.7 | 12.1 | 4.3 | 7.8 |
| | Water [wt %] | 66.9 | 63.8 | 61.4 | 58.4 | 62.0 | 57.0 | 56.7 | 50.2 | 52.7 | 49.2 |
| | Other trace components [wt %] | 2.3 | 2.3 | 2.7 | 2.7 | 2.3 | 2.3 | 2.7 | 2.7 | 3.0 | 3.0 |
| | Total [wt %] | 100.0 | 100.0 | 100.0 | 100.0 | 100.0 | 100.0 | 100.0 | 100.0 | 100.0 | 100.0 |
| Preparation Conditions | Total concentration of Na and K ions derived from component (b) [mol/kg] | 0.11 | 0.55 | 0.12 | 0.55 | 0.8 | 1.51 | 0.8 | 1.7 | 0.61 | 1.1 |
| | Addition order | a | a | a | a | a | a | a | a | a | a |
| | Aqueous soln. temp. when dissolving α-SF salt [° C.] | 70-80 | 70-80 | 70-80 | 70-80 | 70-80 | 70-80 | 70-80 | 70-80 | 70-80 | 70-80 |
| | Added water temp. [° C.] | 75 | 75 | 75 | 75 | 75 | 75 | 75 | 75 | 75 | 75 |
| | Initial quantity of water added [%] | 100 | 100 | 100 | 100 | 100 | 100 | 100 | 100 | 100 | 100 |
| | α-SF salt relative addition rate [h⁻¹] | 1.5 | 1.5 | 1.5 | 1.5 | 1.5 | 1.5 | 1.5 | 1.5 | 1.5 | 1.5 |
| Evaluation | Max. required stirring power [W] | 10 | 10 | 50 | 50 | 10 | 10 | 12 | 15 | 50 | 15 |
| | Aqueous soln. final viscosity [Pa · s] | 0.5 | 0.5 | 17.0 | 15.0 | 0.5 | 0.4 | 1.0 | 1.5 | 9.0 | 2.7 |
| | Adhesion to stirring impeller/shaft | A | A | A | A | A | A | A | A | A | A |
| | Overall evaluation | A | A | C | C | A | A | A | A | C | A |

*The amount of sodium sulfate is only the amount carried over from the α-SF salt flakes, and additional inorganic sodium salt or inorganic potassium salt was not added.

TABLE 2

| | | Examples | | | | | | | | | |
|---|---|---|---|---|---|---|---|---|---|---|---|
| | | 11 | 12 | 13 | 14 | 15 | 16 | 17 | 18 | 19 | 20 |
| Form of solid α-SF salt-containing product | | Flakes | Flakes | Flakes | Flakes | Flakes | Flakes | Flakes | Flakes | Flakes | Flakes |
| Composition | MES [wt %] | 38.4 | 38.4 | 43.2 | 43.2 | 43.2 | 43.2 | 48.0 | 48.0 | 48.0 | 48.0 |
| | di-Na salt [wt %] | 1.6 | 1.6 | 1.8 | 1.8 | 1.8 | 1.8 | 2.0 | 2.0 | 2.0 | 2.0 |
| | Sodium sulfate [wt %] | 9.2 | 12.1 | 4.3 | 6.4 | 7.8 | 12.1 | 4.3 | 5.7 | 7.8 | 10.7 |
| | Water [wt %] | 47.8 | 44.9 | 47.3 | 45.2 | 43.8 | 39.5 | 41.9 | 40.5 | 38.4 | 35.5 |
| | Other trace components [wt %] | 3.0 | 3.0 | 3.4 | 3.4 | 3.4 | 3.4 | 3.8 | 3.8 | 3.8 | 3.8 |
| | Total [wt %] | 100.0 | 100.0 | 100.0 | 100.0 | 100.0 | 100.0 | 100.0 | 100.0 | 100.0 | 100.0 |
| Preparation Conditions | Total concentration of Na and K ions derived from component (b) [mol/kg] | 1.3 | 1.7 | 0.61 | 0.9 | 1.1 | 1.7 | 0.61 | 0.8 | 1.1 | 1.51 |
| | Addition order | a | a | a | a | a | a | a | a | a | a |
| | Aqueous soln. temp. when dissolving α-SF salt [° C.] | 70-80 | 70-80 | 70-80 | 70-80 | 70-80 | 70-80 | 70-80 | 70-80 | 70-80 | 70-80 |
| | Added water temp. [° C.] | 75 | 75 | 75 | 75 | 75 | 75 | 75 | 75 | 75 | 75 |
| | Initial quantity of water added [%] | 100 | 100 | 100 | 100 | 100 | 100 | 100 | 100 | 100 | 100 |
| | α-SF salt relative addition rate [h$^{-1}$] | 1.5 | 1.5 | 1.5 | 1.5 | 1.5 | 1.5 | 1.5 | 1.5 | 1.5 | 1.5 |
| Evaluation | Max. required stirring power [W] | 15 | 15 | 50 | 15 | 15 | 15 | 50 | 20 | 20 | 20 |
| | Aqueous soln. final viscosity [Pa · s] | 1.6 | 1.7 | 10.0 | 4.6 | 3.2 | 5.2 | 11.5 | 7.2 | 7.0 | 10.0 |
| | Adhesion to stirring impeller/shaft | A | A | A | A | A | A | A | A | A | A |
| | Overall evaluation | A | A | C | A | A | A | C | A | A | A |

TABLE 3

| | | Examples | | | | | | | | | |
|---|---|---|---|---|---|---|---|---|---|---|---|
| | | 21 | 22 | 23 | 24 | 25 | 26 | 27 | 28 | 29 | 30 |
| Form of solid α-SF salt-containing product | | Flakes | Flakes | Flakes | Flakes | Flakes | Flakes | Flakes | Flakes | Flakes | Flakes |
| Composition | MES [wt %] | 52.8 | 52.8 | 52.3 | 28.8 | 28.8 | 33.6 | 33.6 | 38.4 | 38.4 | 43.2 |
| | di-Na salt [wt %] | 2.2 | 2.2 | 2.2 | 1.2 | 1.2 | 1.4 | 1.4 | 1.6 | 1.6 | 1.8 |
| | Sodium sulfate [wt %] | 4.3 | 6.4 | 9.2 | 17.8 | 20.6 | 15.6 | 19.0 | 14.9 | 17.8 | 14.2 |
| | Water [wt %] | 36.5 | 34.4 | 31.6 | 49.9 | 47.1 | 46.7 | 43.3 | 42.1 | 39.2 | 37.4 |
| | Other trace components [wt %] | 4.2 | 4.2 | 4.2 | 2.3 | 2.3 | 2.7 | 2.7 | 3.0 | 3.0 | 3.4 |
| | Total [wt %] | 100.0 | 100.0 | 100.0 | 100.0 | 100.0 | 100.0 | 100.0 | 100.0 | 100.0 | 100.0 |
| Preparation Conditions | Total concentration of Na and K ions derived from component (b) [mol/kg] | 0.61 | 0.9 | 1.3 | 2.51 | 2.9 | 2.2 | 2.68 | 2.1 | 2.51 | 2.0 |
| | Addition order | a | a | a | a | a | a | a | a | a | a |
| | Aqueous soln. temp. when dissolving α-SF salt [° C.] | 70-80 | 70-80 | 70-80 | 70-80 | 70-80 | 70-80 | 70-80 | 70-80 | 70-80 | 70-80 |
| | Added water temp. [° C.] | 75 | 75 | 75 | 75 | 75 | 75 | 75 | 75 | 75 | 75 |
| | Initial quantity of water added [%] | 100 | 100 | 100 | 100 | 100 | 100 | 100 | 100 | 100 | 100 |
| | α-SF salt relative addition rate [h$^{-1}$] | 1.5 | 1.5 | 1.5 | 1.5 | 1.5 | 1.5 | 1.5 | 1.5 | 1.5 | 1.5 |
| Evaluation | Max. required stirring power [W] | 50 | 50 | 50 | 10 | 50 | 15 | 50 | 40 | 50 | 40 |
| | Aqueous soln. final viscosity [Pa · s] | 17.0 | 15.0 | 21.0 | 0.8 | 0.8 | 2.0 | 3.0 | 6.6 | 7.3 | 11.0 |
| | Adhesion to stirring impeller/shaft | B | B | B | A | A | A | A | A | A | A |
| | Overall evaluation | C | C | C | A | C | A | C | B | C | B |

TABLE 4

|  |  | Examples | | | Comparative Examples | | | | | | |
| --- | --- | --- | --- | --- | --- | --- | --- | --- | --- | --- | --- |
|  |  | 31 | 32 | 33 | 1 | 2 | 3 | 4 | 5 | 6 | 7 |
| Form of solid α-SF salt-containing product | | Flakes | Flakes | Flakes | Flakes | Flakes | Flakes | Flakes | Flakes | Flakes | Flakes |
| Composition | MES [wt %] | 43.2 | 48.0 | 52.8 | 38.4 | 38.4 | 57.6 | 57.6 | 57.6 | 57.6 | 28.8 |
|  | di-Na salt [wt %] | 1.8 | 2.0 | 2.2 | 1.6 | 1.6 | 2.4 | 2.4 | 2.4 | 2.4 | 1.2 |
|  | Sodium sulfate [wt %] | 15.9 | 14.4 | 12.8 | 1.0* | 3.9 | 4.3 | 6.4 | 9.2 | 12.8 | 22.7 |
|  | Water [wt %] | 35.7 | 31.8 | 28.0 | 56.0 | 53.0 | 31.1 | 29.0 | 26.2 | 22.6 | 45.0 |
|  | Other trace components [wt %] | 3.4 | 3.8 | 4.2 | 3.0 | 3.0 | 4.6 | 4.6 | 4.6 | 4.6 | 2.3 |
|  | Total [wt %] | 100.0 | 100.0 | 100.0 | 100.0 | 100.0 | 100.0 | 100.0 | 100.0 | 100.0 | 100.0 |
| Preparation Conditions | Total concentration of Na and K ions derived from component (b) [mol/kg] | 2.24 | 2.02 | 1.8 | 0.14 | 0.55 | 0.61 | 0.9 | 1.3 | 1.8 | 3.2 |
|  | Addition order | a | a | a | a | a | a | a | a | a | a |
|  | Aqueous soln. temp. when dissolving α-SF salt [° C.] | 70-80 | 70-80 | 70-80 | 70-80 | 70-80 | 70-80 | 70-80 | 70-80 | 70-80 | 70-80 |
|  | Added water temp. [° C.] | 75 | 75 | 75 | 75 | 75 | 75 | 75 | 75 | 75 | 75 |
|  | Initial quantity of water added [%] | 100 | 100 | 100 | 100 | 100 | 100 | 100 | 100 | 100 | 100 |
|  | α-SF salt relative addition rate [h$^{-1}$] | 1.5 | 1.5 | 1.5 | 1.5 | 1.5 | 1.5 | 1.5 | 1.5 | 1.5 | 1.5 |
| Evaluation | Max. required stirring power [W] | 50 | 50 | 50 | 70 | 70 | 70 | 70 | 70 | 70 | 60 |
|  | Aqueous soln. final viscosity [Pa · s] | 15.0 | 21.0 | 24.0 | 30.0 | 31.0 | 36.0 | 29.0 | 28.0 | 28.0 | 0.9 |
|  | Adhesion to stirring impeller/shaft | A | A | A | C | C | C | C | C | C | C |
|  | Overall evaluation | C | C | C | D | D | D | D | D | D | D |

*The amount of sodium sulfate is only the amount carried over from the α-SF salt flakes, and additional inorganic sodium salt or inorganic potassium salt was not added.

TABLE 5

|  |  | Comparative Examples | | | |
| --- | --- | --- | --- | --- | --- |
|  |  | 8 | 9 | 10 | 11 |
| Form of solid α-SF salt-containing product | | Flakes | Flakes | Flakes | Flakes |
| Composition | MES [wt %] | 38.4 | 48.0 | 57.6 | 43.2 |
|  | di-Na salt [wt %] | 1.6 | 2.0 | 2.4 | 1.8 |
|  | Sodium sulfate [wt %] | 20.6 | 17.0 | 14.2 | 7.8 |
|  | Water [wt %] | 36.4 | 29.2 | 21.2 | 43.8 |
|  | Other trace components [wt %] | 3.0 | 3.8 | 4.6 | 3.4 |
|  | Total [wt %] | 100.0 | 100.0 | 100.0 | 100.0 |
| Preparation Conditions | Total concentration of Na and K ions derived from component (b) [mol/kg] | 2.9 | 2.39 | 2.0 | 1.1 |
|  | Addition order | a | a | a | a |
|  | Aqueous soln. temp. when dissolving α-SF salt [° C.] | 70-80 | 70-80 | 70-80 | 40-50 |
|  | Added water temp. [° C.] | 75 | 75 | 75 | 45 |
|  | Initial quantity of water added [%] | 100 | 100 | 100 | 100 |
|  | α-SF salt relative addition rate [h$^{-1}$] | 1.5 | 1.5 | 1.5 | 1.5 |
| Evaluation | Max. required stirring power [W] | 60 | 70 | 70 | Undissolvable |
|  | Aqueous soln. final viscosity [Pa · s] | 10.0 | 30.0 | 40.0 | — |
|  | Adhesion to stirring impeller/shaft | C | C | C | — |
|  | Overall evaluation | D | D | D | — |

TABLE 6

|  | Examples | | | | | |
| --- | --- | --- | --- | --- | --- | --- |
|  | 31 | 35 | 36 | 37 | 38 | 39 |
| Form of solid α-SF salt-containing product | Flakes | Flakes | Flakes | Flakes | Flakes | Flakes |
| Composition MES [wt %] | 28.8 | 38.4 | 43.2 | 43.2 | 48.0 | 52.8 |
| di-Na salt [wt %] | 1.2 | 1.6 | 1.8 | 1.8 | 2.0 | 2.2 |
| Sodium sulfate [wt %] | 0.8 | 1.0 | 1.1 | 1.1 | 1.3 | 1.1 |
| Sodium chloride [wt %] | 2.3 | 5.6 | 5.5 | 9.0 | 5.1 | 9.1 |
| Potassium sulfate [wt %] | — | — | — | — | — | — |
| Potassium chloride [wt %] | — | — | — | — | — | — |
| Sodium sulfite [wt %] | — | — | — | — | — | — |
| Potassium sulfite [wt %] | — | — | — | — | — | — |
| Potassium nitrate [wt %] | — | — | — | — | — | — |
| Potassium bicarbonate [wt %] | — | — | — | — | — | — |

TABLE 6-continued

|  |  | Examples | | | | | |
| --- | --- | --- | --- | --- | --- | --- | --- |
|  |  | 31 | 35 | 36 | 37 | 38 | 39 |
|  | Water [wt %] | 64.6 | 50.4 | 45.0 | 41.5 | 39.5 | 30.0 |
|  | Other trace components [wt %] | 2.3 | 3.0 | 3.4 | 3.4 | 3.8 | 4.2 |
|  | Total [wt %] | 100.0 | 100.0 | 100.0 | 100.0 | 100.0 | 100.0 |
| Preparation Conditions | Total concentration of Na and K ions derived from component (b) [mol/kg] | 0.5 | 1.1 | 1.1 | 1.7 | 1.1 | 1.8 |
|  | Addition order | a | a | a | a | a | a |
|  | Aqueous soln. temp. when dissolving α-SF salt [° C.] | 70-80 | 70-80 | 70-80 | 70-80 | 70-80 | 70-80 |
|  | Added water temp. [° C.] | 75 | 75 | 75 | 75 | 75 | 75 |
|  | Initial quantity of water added [%] | 100 | 100 | 100 | 100 | 100 | 100 |
|  | α-SF salt relative addition rate [h$^{-1}$] | 1.5 | 1.5 | 1.5 | 1.5 | 1.5 | 1.5 |
| Evaluation | Max. required stirring power [W] | 10 | 15 | 15 | 15 | 20 | 50 |
|  | Aqueous soln. final viscosity [Pa · s] | 0.4 | 0.5 | 0.6 | 0.6 | 1.5 | 5.5 |
|  | Adhesion to stirring impeller/shaft | A | A | A | A | A | B |
|  | Overall evaluation | A | A | A | A | A | C |

TABLE 7

|  |  | Examples | | | | | |
| --- | --- | --- | --- | --- | --- | --- | --- |
|  |  | 40 | 41 | 42 | 43 | 44 | 45 |
| Form of solid α-SF salt-containing product |  | Flakes | Flakes | Flakes | Flakes | Flakes | Flakes |
| Composition | MES [wt %] | 43.2 | 43.2 | 43.2 | 43.2 | 43.2 | 43.2 |
|  | di-Na salt [wt %] | 1.8 | 1.8 | 1.8 | 1.8 | 1.8 | 1.8 |
|  | Sodium sulfate [wt %] | 1.1 | 1.1 | 1.1 | 1.1 | 1.1 | 1.1 |
|  | Sodium chloride [wt %] | — | — | — | — | — | — |
|  | Potassium sulfate [wt %] | 8.2 | — | — | — | — | — |
|  | Potassium chloride [wt %] | — | 7.0 | — | — | — | — |
|  | Sodium sulfite [wt %] | — | — | 5.9 | — | — | — |
|  | Potassium sulfite [wt %] | — | — | — | 7.5 | — | — |
|  | Potassium nitrate [wt %] | — | — | — | — | 9.5 | — |
|  | Potassium bicarbonate [wt %] | — | — | — | — | — | 9.4 |
|  | Water [wt %] | 42.3 | 43.5 | 44.6 | 43.0 | 41.0 | 41.1 |
|  | Other trace components [wt %] | 3.4 | 3.4 | 3.4 | 3.4 | 3.4 | 3.4 |
|  | Total [wt %] | 100.0 | 100.0 | 100.0 | 100.0 | 100.0 | 100.0 |
| Preparation Conditions | Total concentration of Na and K ions derived from component (b) [mol/kg] | 1.1 | 1.1 | 1.1 | 1.1 | 1.1 | 1.1 |
|  | Addition order | a | a | a | a | a | a |
|  | Aqueous soln. temp. when dissolving α-SF salt [° C.] | 70-80 | 70-80 | 70-80 | 70-80 | 70-80 | 70-80 |
|  | Added water temp. [° C.] | 75 | 75 | 75 | 75 | 75 | 75 |
|  | Initial quantity of water added [%] | 100 | 100 | 100 | 100 | 100 | 100 |
|  | α-SF salt relative addition rate [h$^{-1}$] | 1.5 | 1.5 | 1.5 | 1.5 | 1.5 | 1.5 |
| Evaluation | Max. required stirring power [W] | 15 | 15 | 15 | 15 | 20 | 50 |
|  | Aqueous soln. final viscosity [Pa · s] | 3.1 | 0.6 | 3.4 | 3.2 | 2.4 | 3.0 |
|  | Adhesion to stirring impeller/shaft | A | A | A | A | A | A |
|  | Overall evaluation | A | A | A | A | A | A |

TABLE 8

|  |  | Examples | | | | | | | | | | |
| --- | --- | --- | --- | --- | --- | --- | --- | --- | --- | --- | --- | --- |
|  |  | 46 | 47 | 48 | 49 | 50 | 51 | 52 | 53 | 54 | 55 | 56 |
| Form of solid α-SF salt-containing product |  | Flakes | Flakes | Flakes | Flakes | Flakes | Flakes | Pellet | Powder | Flakes | Flakes | Flakes |
| Composition | MES [wt %] | 43.2 | 43.2 | 43.2 | 43.2 | 43.2 | 43.2 | 43.2 | 43.2 | 43.2 | 48.0 | 43.2 |
|  | di-Na salt [wt %] | 1.8 | 1.8 | 1.8 | 1.8 | 1.8 | 1.8 | 1.8 | 1.8 | 1.8 | 2.0 | 1.8 |
|  | Sodium sulfate [wt %] | 7.8 | 7.8 | 7.8 | 7.8 | 7.8 | 7.8 | 7.8 | 7.8 | 7.8 | 5.7 | 7.8 |
|  | Water [wt %] | 43.8 | 43.8 | 43.8 | 43.8 | 43.8 | 43.8 | 43.8 | 43.8 | 43.8 | 40.5 | 43.8 |
|  | Other trace components [wt %] | 3.4 | 3.4 | 3.4 | 3.4 | 3.4 | 3.4 | 3.4 | 3.4 | 3.4 | 3.8 | 3.4 |
|  | Total [wt %] | 100.0 | 100.0 | 100.0 | 100.0 | 100.0 | 100.0 | 100.0 | 100.0 | 100.0 | 100.0 | 100.0 |

TABLE 8-continued

| | | Examples | | | | | | | | | | |
|---|---|---|---|---|---|---|---|---|---|---|---|---|
| | | 46 | 47 | 48 | 49 | 50 | 51 | 52 | 53 | 54 | 55 | 56 |
| Preparation Conditions | Total concentration of Na and K ions derived from component (b) [mol/kg] | 1.1 | 1.1 | 1.1 | 1.1 | 1.1 | 1.1 | 1.1 | 1.1 | 1.1 | 0.8 | 1.1 |
| | Addition order | a | a | b | b | a | a | a | a | c | d | e |
| | Aqueous soln. temp. when dissolving α-SF salt [° C.] | 50-60 | 60-70 | 70-80 | 70-80 | 70-80 | 70-80 | 70-80 | 70-80 | 70-80 | 70-80 | 70-80 |
| | Added water temp. [° C.] | 55 | 65 | 75 | 75 | 75 | 75 | 75 | 75 | 75 | 75 | 75 |
| | Initial quantity of water added [%] | 100 | 100 | 55 | 60 | 100 | 100 | 100 | 100 | 100 | 100 | 20 |
| | α-SF salt relative addition rate [h$^{-1}$] | 1.5 | 1.5 | 1.5 | 1.5 | 8 | 5 | 1.5 | 1.5 | 1.5 | 1.5 | 1.5 |
| Evaluation | Max. required stirring power [W] | 50 | 40 | 50 | 40 | 50 | 40 | 15 | 15 | 15 | 20 | 15 |
| | Aqueous soln. final viscosity [Pa·s] | 10.0 | 8.0 | 3.5 | 3.5 | 3.5 | 3.4 | 3.3 | 3.4 | 3.0 | 7.2 | 3.2 |
| | Adhesion to stirring impeller/shaft | A | A | A | A | A | A | A | A | A | A | A |
| | Overall evaluation | C | B | C | B | C | B | A | A | A | A | A |

TABLE 9

| | | Comparative Examples | |
|---|---|---|---|
| | | 12 | 13 |
| Form of solid α-SF salt-containing product | | Flakes | Flakes |
| Composition | MES [wt %] | 43.2 (38.4) ** | 48.0 (38.4) ** |
| | di-Na salt [wt %] | 1.8 (1.6) ** | 2.0 (1.6) ** |
| | Sodium sulfate [wt %] | 7.8 (3.1) ** | 5.7 (3.7) ** |
| | Water [wt %] | 43.8 (53.9) ** | 40.5 (53.3) ** |
| | Other trace components [wt %] | 3.4 (3.0) ** | 3.8 (3.0) ** |
| | Total [wt %] | 100.0 (100.0) ** | 100.0 (100.0) ** |
| Preparation Conditions | Total concentration of Na and K ions derived from component (b) [mol/kg] | 1.10 (0.44) ** | 0.80 (0.52) ** |
| | Addition order | f | g |
| | Aqueous soln. temp. when dissolving α-SF salt [° C.] | 70-80 | 70-80 |
| | Added water temp. [° C.] | 75 | 75 |
| | Initial quantity of water added [%] | 100 | 100 |
| | α-SF salt relative addition rate [h$^{-1}$] | 1.5 | 1.5 |
| Evaluation | Max. required stirring power [W] | 70 | 70 |
| | Aqueous soln. final viscosity [Pa·s] | 30.0 | 31.0 |
| | Adhesion to stirring impeller/shaft | C | C |
| | Overall evaluation | D | D |

** Figures in parentheses indicate aqueous solution composition when preparation discontinued.

TABLE 10

| | | Formulation Examples 1-3 |
|---|---|---|
| Spray-dried granule composition [%] | α-SF-Na | 10 |
| | LAS-Na | 10 |
| | STPP | 20 |
| | Sodium polyacrylate | 2 |
| | Sodium sulfate | 26.6 |
| | Sodium carbonate | 25 |
| | Water | 5 |
| | Other trace components | 1.4 |
| | Total | 100 |
| Slurry temperature [° C.] | | 38 |
| Spray-dried granule mean particle diameter [μm] | | 270-300 |
| Spray-dried granule bulk density [kg/L] | | 0.36-0.39 |

TABLE 11

| | | Formulation Example 4 |
|---|---|---|
| Spray-dried granule composition [%] | a) α-SF-Na | 8 |
| | b) LAS-Na | 8 |
| | c) STPP | 10 |
| | d) Sodium silicate | 10 |
| | Soap | 4 |
| | Sodium acrylate/maleate copolymer | 2 |
| | Sodium sulfate | 22.7 |
| | Sodium carbonate | 8 |
| | Potassium carbonate | 7 |
| | Sodium sulfite | 4 |
| | Zeolite | 10 |
| | Fluorescent agent | 0.2 |
| | Water | 5 |
| | Other trace components | 1.1 |
| | Total | 100 |
| Slurry temperature [° C.] | | 65 |
| Spray-dried granule mean particle diameter [μm] | | 290 |
| Spray-dried granule bulk density [kg/L] | | 0.43 |

Figure 2:
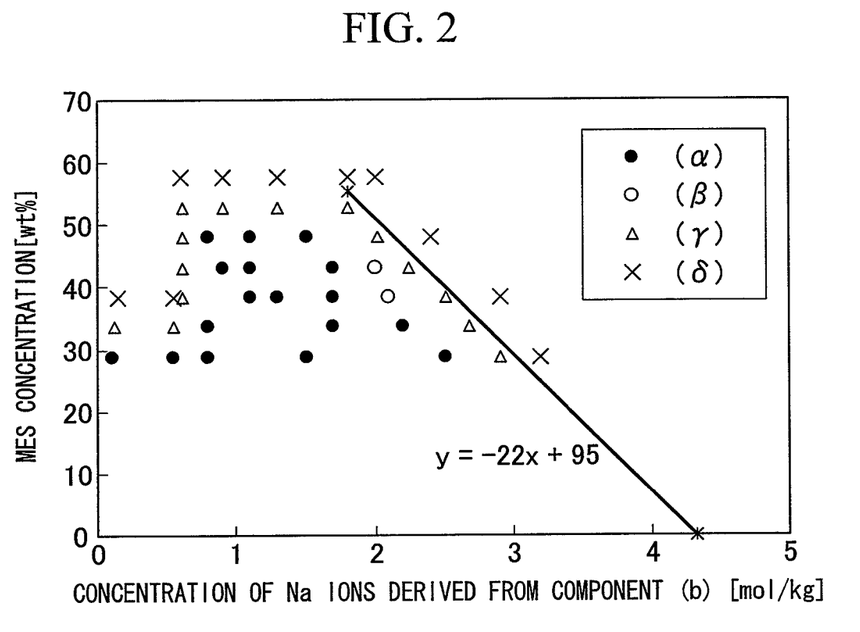
FIG. 2 is a graph indicating the relationship among MES concentration, Na ion concentration derived from component (b) and overall evaluation judgment results in Examples 1 to 33 and Comparative Examples 1 to 10.

FIG. 2 is a graph of the overall evaluations of the corresponding Examples 1 to 33 and Comparative Examples 1 to 10 in which MES concentration (wt %) is plotted on the vertical axis and concentration of sodium ions derived from component (b) (mol/kg) is plotted on the horizontal axis. In FIG. 2, (α) in the legend of the graph represents an overall evaluation of "A", (β) represents an overall evaluation of "B", (γ) represents an overall evaluation of "C"), and (δ) represents an overall evaluation of "D". The order of addition of the preparation conditions was that of "a" in all of Examples 1 to 33 and Comparative Examples 1 to 10. As shown in FIG. 2, overall evaluation can be seen to be favorable when the concentration of sodium ions derived from component (b) is 0.55 mol/kg to less than 1.8 mol/kg and the MES concentration is greater than 35% by weight to 55% by weight. In addition, overall evaluation can be seen to be favorable in the range that satisfies the following formula (1) when the concentration of sodium ions derived from component (b) is 1.8 mol/kg or more:

$$y \leq -22x+95 \qquad (1)$$

(wherein, y represents the concentration of component (a) [wt %], and x represents the total concentration of sodium ions and potassium ions derived from component (b) [mol/kg]).

As is indicated in Tables 1 to 4 and Tables 6 to 8, the aqueous α-SF salt solutions of Examples 1 to 56 produced according to the production method of an aqueous α-SF salt solution of the present invention were all evaluated as having an overall evaluation of "C" or better, thereby demonstrating properties able to accommodate actual production. In contrast, as shown in Tables 4, 5 and 9, Comparative Examples 1 to 13 all demonstrated values for maximum requiring stirring power in excess of 55 W, and imparted a considerable burden on the dissolving apparatus. In addition, adhesion was evaluated as "D", thereby demonstrating properties that were unable to accommodate actual production. Namely, Examples 1 to 56 were confirmed to enable the production of an aqueous α-SF salt solution that has lower viscosity and greater fluidity in comparison with Comparative Examples 1 to 13.

In addition, in a comparison of Examples 1 to 56 and Comparative Examples 12 and 13, since the relationship between total concentration of sodium and potassium ions derived from an inorganic salt and the concentration of MES serving as α-SF salt was maintained throughout the production process, aqueous α-SF solutions having fluidity and low viscosity were determined to be able to be produced.

In a comparison of Examples 15 and 36 with Examples 40 to 45, it was determined that aqueous α-SF salt solutions having production adaptability and relatively low viscosity can be produced irrespective of the type of inorganic sodium salt or inorganic potassium salt added provided the production conditions of the present invention are satisfied.

INDUSTRIAL APPLICABILITY

According to the production method of an aqueous α-SF salt solution of the present invention, an aqueous α-SF salt solution can be used that facilitates dissolution of a solid α-SF salt in water, maintains fluidity and has superior production adaptability.

BRIEF DESCRIPTION OF THE REFERENCE SYMBOLS

10 Dissolving tank
12 Body
14 Jacket
20 Stirring unit
22 Stirring impeller
24 Stirring shaft
30 Drive unit
32 Torque meter
40 Dissolving tank
41 Mixing vessel
42 Drive unit
43 Stirring shaft
44 Inclined paddle impeller
45 Inclined paddle impeller
46 Baffle plate
47 Jacket

We claim:

1. A method for producing an aqueous α-sulfo fatty acid ester salt solution in which a solid component (a) in the form of an α-sulfo fatty acid alkyl ester salt and a component (b) in the form of an inorganic sodium salt and/or inorganic potassium salt are dissolved in a solvent in the form of water; wherein, the solid component (a) is dissolved in the solvent in the form of water under temperature conditions of 50° C. or higher while maintaining the following condition (i) or (ii):

(i): the concentration of the component (a) is 35% by weight or less in the case where the total concentration of sodium ions and potassium ions derived from the component (b) is less than 0.55 mol/kg, or (ii) the concentration of the component (a) is 55% by weight or less in the case where the total concentration of sodium ions and potassium ions derived from the component (b) is 0.55 mol/kg to less than 1.8 mol/kg.

2. The method for producing an aqueous α-sulfo fatty acid ester salt solution according to claim 1, wherein the solid component (a) is dissolved in a solvent while maintaining the following condition (iii):

(iii) the concentration of the component (a) is within a range represented by the following formula (1) in the case where the total concentration of sodium ions and potassium ions derived from the component (b) is 1.8 mol/kg to less than 4.3 mol/kg:

$$y \leq -22x+95 \qquad (1)$$

wherein, y represents the concentration of the component (a) (wt %), and x represents the total concentration of sodium ions and potassium ions derived from the component (b) (mol/kg).

3. The method for producing an aqueous α-sulfo fatty acid ester salt solution according to claim 1, wherein 20% by weight or more of the solvent is used as an initial solvent, and after dissolving at least a portion of the solid component (a) and component (b) in the initial solvent, the remainder of the solvent is added, and finally the remainder of the solid component (a) and component (b) are added.

4. The method for producing an aqueous α-sulfo fatty acid ester salt solution according to claim 1, wherein the relative addition rate of the solid component (a) to the solvent as represented by the following formula (2) is $0.1\ h^{-1}$ to less than $10\ h^{-1}$:

Relative addition rate of solid component (*a*)=addition rate of solid component (*a*) (kg/h)/final amount of aqueous α-sulfo fatty acid alkyl ester salt solution (kg)  (2).

* * * * *